United States Patent [19]
Bosmans

[11] Patent Number: 5,854,261
[45] Date of Patent: Dec. 29, 1998

[54] PROKINETIC COMPOUNDS

[75] Inventor: Jean-Paul René Marie André Bosmans, B-2650 Edegem, Belgium

[73] Assignee: Janssen Pharmaceutica N.V., Belgium

[21] Appl. No.: 894,340

[22] PCT Filed: Feb. 21, 1996

[86] PCT No.: PCT/EP96/00784

§ 371 Date: Aug. 15, 1997

§ 102(e) Date: Aug. 15, 1997

[87] PCT Pub. No.: WO96/26937

PCT Pub. Date: Sep. 6, 1996

[30] Foreign Application Priority Data

Mar. 1, 1995 [EP] European Pat. Off. ............. 95200501

[51] Int. Cl.$^6$ ....................... A61K 31/445; C07D 413/04
[52] U.S. Cl. ........................ 514/320; 514/326; 546/196; 546/209
[58] Field of Search ..................... 546/210, 209, 546/196; 514/326, 320

[56] References Cited

FOREIGN PATENT DOCUMENTS

| 95/32965 | 12/1995 | Japan . |
| 9302677 | 2/1993 | United Kingdom . |
| 94/08995 | 1/1994 | WIPO . |
| 94/08994 | 4/1994 | WIPO . |
| 94/10174 | 5/1994 | WIPO . |

OTHER PUBLICATIONS

International Search Report Application Number PCT/EP96/00784.

Patent Abstracts of Japan, Vol. 18, No. 485(C–1248) Sep. 9, 1994 & JP A 06 157518 (Yamanouchi Pharmaceut Co Ltd), Jun. 3, 1994 in connection with Chemical Abstracts, 1994 Vol. 121 No. 23, p. 1035, No. 280649k.

Chemical Abstracts, 1994 Vol. 121, Chemical Substance Index, part 1 p. 1073cs, col. 3, lines 57–61.

Primary Examiner—Fiona T. Powers
Attorney, Agent, or Firm—Ellen Ciambrone Coletti

[57] ABSTRACT

The present invention concerns novel oxadiazole derivatives of formula (I)

the N-oxide forms, the pharmaceutically acceptable acid addition salts and the stereochemically isomeric forms thereof, wherein $R^1$ is hydrogen or halo; $R^2$ is $C_{1-6}$alkyl, $C_{2-6}$alkenyl or $C_{2-6}$alkynyl; $R^3$ is hydrogen; or $R^2$ and $R^3$ taken together may form a $C_{2-3}$alkanediyl radical wherein one or two hydrogen atoms may be replaced by $C_{1-4}$alkyl; $R^4$ is hydrogen or $C_{1-6}$alkyloxy; X is a bivalent radical of the formula L is a radical of formula -Alk-$R^5$ or -Alk—O—$R^6$, Alk is $C_{1-12}$alkanediyl; $R^5$ is hydrogen, cyano, $C_{1-6}$alkylcarbonyl, $C_{1-6}$alkylsulfinyl, $C_{1-6}$alkylsulfonyl, aryl, arylcarbonyl, tetrahydrofuran, dioxolane, dioxolane substituted with $C_{1-6}$alkyl, dioxane, dioxane substituted with $C_{1-6}$alkyl; $R^6$ is hydrogen, aryl, $C_{1-6}$alkyl, hydroxy$C_{1-6}$alkyl, $C_{1-6}$alkylcarbonyl; aryl is defined as phenyl or phenyl substituted with up to three substituents selected from halo, $C_{1-6}$alkyl or $C_{1-6}$alkyloxy. It further relates to pharmaceutical compositions comprising them, processes for preparing said compounds and compositions, and the use thereof as a medicine, in particular in the conditions involving a decreased motility of the colon.

19 Claims, No Drawings

PROKINETIC COMPOUNDS

CROSS-REFERENCE TO RELATED APPLICATIONS

This application is a 371 based upon PCT Application Serial No. PCT/EP96/00784, filed Feb. 21, 1996, which claims priority from European Patent Application Serial No. 95.200.501.5, filed on Mar. 1, 1995.

The present invention concerns novel prokinetic oxadiazole derivatives. It further relates to pharmaceutical compositions comprising them, processes for preparing said compounds and compositions, and the use thereof as a medicine, in particular in the conditions involving a decreased motility of the colon.

EP-0,076,530, EP-0,389,037 and EP-0,445,862 disclose N-(4-piperidinyl)benzamide derivatives having gastrointestinal motility stimulating properties. WO-94/12494 describes the use of dimethylbenzofurans and dimethylbenzopyrans as $5\text{-}HT_3$ antagonists. WO 93/02677 describes oxadiazoles as $5\text{-}HT_4$ receptor antagonists. WO 94/08994 describes a number of 1-butyl-4-piperidinylmethyl substituted bicyclic benzoic ester derivatives as $5\text{-}HT_4$ receptor antagonists. WO 94/08995 describes some other 1-butyl-4-piperidinylmethyl substituted bicyclic benzoic ester derivatives as $5\text{-}HT_4$ receptor antagonists. WO 94/10174 discloses N-piperidinyl (benzodioxolane and 1,4-benzodioxane) carboxamide derivatives as $5\text{-}HT_4$ receptor antagonists.

The compounds of the present invention differ from the prior art compounds by the presence of an oxadiazole moiety which is directly bound to the piperidinyl ring. The present compounds unexpectedly show favourable intestinal motility stimulating properties. More in particular, they show motility enhancing effects on the colon.

This invention concerns compounds of formula

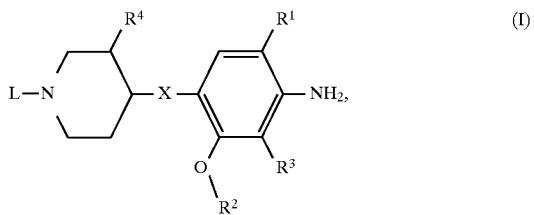

the N-oxide forms, the pharmaceutically acceptable acid addition salts and the stereochemically isomeric forms thereof, wherein:
$R^1$ is hydrogen or halo;
$R^2$ is $C_{1-6}$alkyl, $C_{2-6}$alkenyl or $C_{2-6}$alkynyl;
$R^3$ is hydrogen;
or $R^2$ and $R^3$ taken together may form a $C_{2-3}$alkanediyl radical wherein one or two hydrogen atoms may be replaced by $C_{1-4}$alkyl;
$R^4$ is hydrogen, hydroxy or $C_{1-6}$alkyloxy;
X is a bivalent radical of the formula

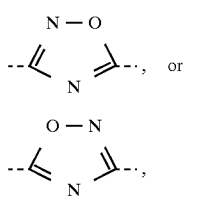

L is a radical of formula:

-Alk-$R^5$ (b),

-Alk—O—$R^6$ (c),

Alk is $C_{1-12}$alkanediyl;
$R^5$ is hydrogen, cyano, $C_{1-6}$alkylcarbonyl, $C_{1-6}$alkylsulfmyl, $C_{1-6}$alkylsulfonyl, aryl, arylcarbonyl, tetrahydrofuran, dioxolane, dioxolane substituted with $C_{1-6}$alkyl, dioxane, dioxane substituted with $C_{1-6}$alkyl;
$R^6$ is hydrogen, aryl, $C_{1-6}$alkyl, hydroxy$C_{1-6}$alkyl, $C_{1-6}$alkylcarbonyl;
aryl is defined as phenyl or phenyl substituted with up to three substituents selected from halo, $C_{1-6}$alkyl or $C_{1-6}$alkyloxy.

As used in the foregoing definitions halo is generic to fluoro, chloro, bromo and iodo; $C_{1-4}$alkyl defines straight and branched saturated hydrocarbon radicals having from 1 to 4 carbon atoms such as, for example, methyl, ethyl, propyl, butyl, 1-methylethyl, 2-methylpropyl and the like; $C_{1-6}$alkyl defines $C_{1-4}$alkyl and the higher homologues having 5 or 6 carbon atoms such as, for example, pentyl, hexyl and the like; $C_{2-6}$alkenyl defines straight or branched hydrocarbon radicals having one double bond and having from 2 to 6 carbon atoms such as, for example, ethenyl, 2-propenyl, 3-butenyl, 2-butenyl, 2-pentenyl, 3-methyl-2-butenyl and the like; $C_{2-6}$alkynyl defines straight or branched hydrocarbon radicals having one triple bond and having 2 to 6 carbon atoms such as, for example, ethynyl, 2-propynyl, 3-butynyl, 2-butynyl, 2-pentynyl, 3-methyl-2-butynyl and the like; $C_{2-3}$alkanediyl defines bivalent straight or branched hydrocarbon radicals containing from 2 to 3 carbon atoms such as, for example, 1,2-ethanediyl, 1,3-propanediyl and the like; $C_{1-12}$alkanediyl defines $C_{2-3}$alkanediyl, the lower homologue, i.e. 1,1-methanediyl, and the higher homologues having from 4 to 12 carbon atoms such as, for example, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. Conversely the salt form can be converted by treatment with alkali into the free base form.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated radicals may have either the cis- or trans-configuration.

Stereochemically isomeric forms of the compounds of formula (I) are obviously intended to be embraced within the scope of this invention.

The N-oxide forms of the compounds of formula (I) are meant to comprise those compounds of formula (I) wherein one or several nitrogen atoms are oxidized to the so-called N-oxide, particularly those N-oxides wherein the piperidine-nitrogen is N-oxidized.

Whenever used hereinafter, the term "compounds of formula (I)" is meant to also include the N-oxide forms, the pharmaceutically acceptable acid addition salts and all stereochemically isomeric forms thereof.

Interesting compounds are those compounds of formula (I) wherein $R^4$ is hydrogen.

Another group of interesting compounds encompasses those compounds of formula (I) wherein $R^1$ is halo, preferably chloro.

Also interesting compounds are those compounds of formula (I) wherein L is a radical of formula (b) wherein $R^5$ is preferably cyano or tetrahydrofuran; or L is a radical of formula (c) wherein $R^6$ is preferably $C_{1-6}$alkyl, hydroxy$C_{1-6}$alkyl or phenyl substituted with an halogen.

Particular compounds are those wherein $R^2$ and $R^3$ taken together form a $C_{2-3}$alkanediyl radical, preferably an ethanediyl radical, wherein one or two hydrogen atoms may be replaced by $C_{1-4}$alkyl.

Also particular compounds are those compounds wherein $R^2$ is $C_{1-6}$alkyl, suitably methyl, and $R^3$ is hydrogen.

Preferred compounds are those compounds of formula (I) wherein $R^1$ is chloro; $R^2$ is methyl; $R^3$ and $R^4$ are hydrogen; L is a radical of formula (b) wherein $R^5$ is tetrahydrofuran, or a radical of formula (c) wherein $R^6$ is 4-fluorophenyl.

Also preferred compounds are those compounds of formula (I) wherein $R^1$ is chloro; $R^2$ and $R^3$ taken together form an ethanediyl radical geminally disubstituted with methyl; $R^4$ is hydrogen; and L is a radical of formula (b) wherein $R^5$ is cyano.

Other preferred compounds are those compounds of formula (I) wherein $R^1$ is chloro; $R^2$ and $R^3$ taken together form an ethanediyl radical; $R^4$ is hydrogen; and L is a radical of formula (c) wherein $R^6$ is methyl.

Most preferred compounds are:
2-chloro-5-methoxy-4-[3-[1-[(tetrahydro-2-furanyl) methyl]-4-piperidinyl]-1,2,4-oxadiazol-5-yl] benzenamine;
5-chloro-2,3-dihydro-7-[3-[1-(3-methoxypropyl)-4-piperidinyl]-1,2,4-oxadiazol-5-yl]4-benzofuranamine;
5-chloro-2,3-dihydro-7-[5-[1-(3-methoxypropyl)-4-piperidinyl]-1,2,4-oxadiazol-3-yl]-4-benzofuranamine;
the pharmaceutically acceptable acid addition salts and the stereochemically isomeric forms thereof.

In order to simplify the structural representations of the compounds of formula (I) and certain starting materials and intermediates thereof, the radical

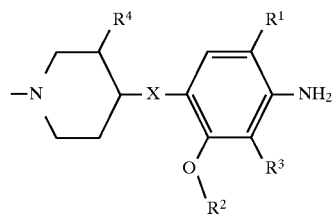

will hereinafter be represented by the symbol D.

In the following preparations, the reaction products may be isolated from the reaction mixture and, if necessary, further purified according to methodologies generally known in the art such as, for example, extraction, distillation, crystallization, trituration and chromatography.

The compounds of formula (I) may be prepared by N-alkylating a piperidine of formula (II), wherein D is as defined above, with an intermediate of formula (III), wherein $W^1$ is an appropriate leaving group such as, for example, halo, e.g. chloro, bromo or iodo, or a sulfonyloxy group, e.g. methanesulfonyloxy, 4-methylbenzenesulfonyloxy and the like leaving groups. The N-alkylation reaction of (II) with (III) is conveniently conducted following art-known alkylation procedures.

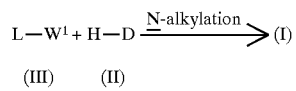

(III)  (II)

The compounds of formula (I) may also be prepared by converting compounds of formula (I) into each other.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. t.butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The intermediates of formula (II), wherein X is a radical of formula (a-1), said intermediates being represented by H-D¹ (II-a-1), may be derived from an appropriately substituted piperidine of formula (IV) with an intermediate carboxylic ester of formula (V), wherein $R^7$ is $C_{1-6}$alkyl, following art-known cyclization procedures, and subsequently removing the protective group P, following art-known procedures. P represents a readily removable protective group such as $C_{1-4}$alkylcarbonyl, $C_{1-4}$alkyloxycarbonyl, phenylmethyl, and the like art-known N-protective groups.

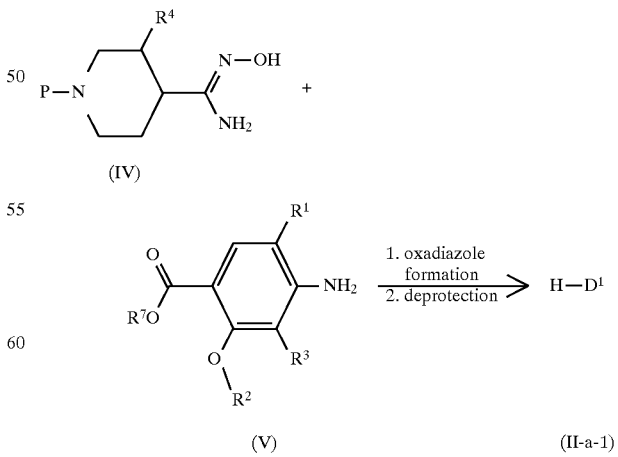

The intermediates of formula (II), wherein X is a radical of formula (a-2), said intermediates being represented by H-D² (II-a-2), may be derived from an appropriately substituted piperidine of formula (VI), wherein R⁷ is $C_{1-6}$alkyl, with an intermediate of formula (VII), following art-known cyclization procedures, and subsequently removing the protective group P, defined as hereinabove, following art-known procedures.

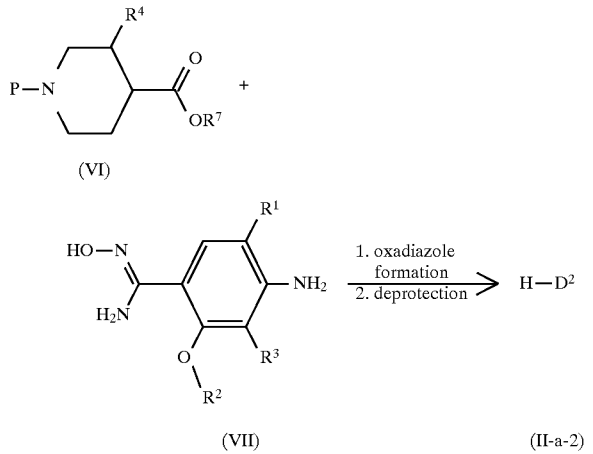

Intermediates of formula (IV) may be prepared by reacting an intermediate of formula (VIII) with hydroxylamine in a reaction-inert solvent and in the presence of a strong base, such as, for example, sodium methoxide.

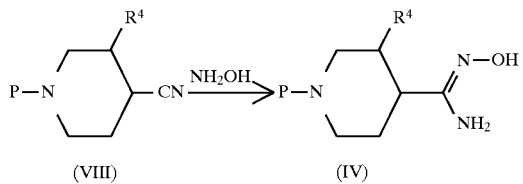

The compounds of formula (I) may also be prepared via oxadiazole formation in an analogous way as is described for intermediates (II-a-1) and (II-a-2).

Intermediate carboxylic esters of formula (V) may be prepared from the corresponding carboxylic acids following art-known ester formation procedures. Said corresponding carboxylic acids are known from, for example, EP-0,076, 530, EP-0,389,037 and EP-0,445 ,862.

The intermediates of formula (VII) may be prepared by dehydrating an intermediate of formula (VIII) using an appropriate dehydrating agent such as, for example, phosphorus pentoxide, phosphorus oxychloride or thionylchloride, and subsequently reacting the thus formed nitrile with hydroxylamine in a reaction-inert solvent and in the presence of a strong base such as, for example, sodium methoxide.

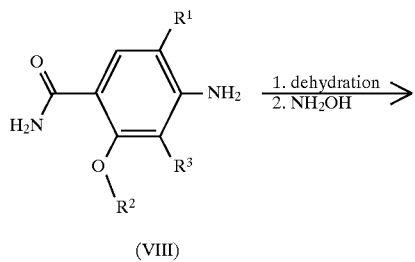

-continued

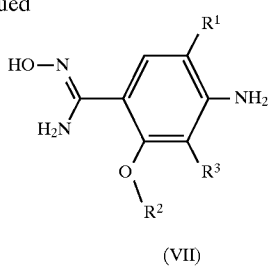

The racemates of the compounds of formula (I), or any of the other intermediates may also be resolved into their optical isomers, by the application of art-known methodologies. Diastereoisomers may be separated by physical separation methods such as selective crystallization and chromatographic techniques, e.g. counter current distribution, and enantiomers may be separated from each other by the selective crystallization of their diastereomeric salts with enantiomerically pure acids or their enantiomerically pure derivatives.

The compounds of formula (I), the N-oxide forms, the pharmaceutically acceptable salts and stereoisomeric forms thereof possess favourable intestinal motility stimulating properties. In particular the present compounds show significant motility enhancing effects on the small and large intestine.

The stimulatory effect of the subject compounds of formula (I) on the motility of the intestinal system, in particular the motility enhancing effects on the colon, may be evidenced by the "Colon Motility in the Conscious Dog" test which is described hereinafter.

In view of their useful intestinal motility enhancing properties, the subject compounds may be formulated into various forms for administration purposes.

As appropriate pharmaceutical compositions there may be cited all compositions usually employed for systemically administering drugs. To prepare the pharmaceutical compositions of this invention, a therapeutically effective amount of the particular compound, optionally in acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of compounds of formula (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the capability of the compounds of the present invention to stimulate the motility of the intestinal system and, in particular their capacity to enhance the motility of the colon, the subject compounds are useful to normalize or to improve the intestinal emptying in subjects suffering from a disturbed motility, e.g. a decreased peristalsis of the small and/or large intestine.

In view of the utility of the compounds of formula (I), it follows that the present invention also provides a method of treating warm-blooded animals suffering from motility disorders of the intestinal system such as, for example, pseudo-obstruction, and in particular impaired colonic transit. Said method comprising the systemic administration of an effective intestinal stimulating amount of a compound of formula (I) to warm-blooded animals. Hence, the use of a compound of formula (I) as medicine is provided, and in particular the use of a compound of formula(I) for the manufacture of a medicine for treating conditions involving a decreased motility of the colon.

Those of skill in the treatment of such motility disorders could determine the effective stimulating amount from the test results presented hereinafter. An effective amount would be from about 0.01 mg/kg to about 10 mg/kg body weight, more preferably from about 0.1 mg/kg to about 5 mg/kg body weight. A method of treatment may also include administering the active ingredient on a regimen of between two to four intakes per day.

The following examples are intended to illustrate and not to limit the scope of the present invention. Hereinafter, "DIPE" means diisopropylether and "RT" means room temperature.

EXPERIMENTAL PART

A. Preparation of intermediate compounds

EXAMPLE 1

Sulfuric acid (18 ml) was added dropwise to cooled methanol (90 ml). 4-Amino-5-chloro-2,3-dihydro-7-benzofurancarboxylic acid (20 g) was added to the mixture which was subsequently stirred and refluxed for 3 hours. The reaction mixture was cooled and alkalized with $CH_3OH$/$NH_3$. The solvent was evaporated and the residue stirred in water. The precipitate was filtered off and washed with water and DIPE. The remaining solid was dried, yielding 17.2 g (81%) of methyl 4-amino-5-chloro-2,3-di-hydro-7-benzofurancarboxylate (intermediate 1; mp. 135.4° C.).

EXAMPLE 2

Ethanol (150 ml) was added to a solution of hydroxylamine hydrochloride (17.25 g) in water (48 ml). Ethyl 4-cyano-1-piperidinecarboxylate (45 g) was added and the mixture was cooled. Sodium methoxide (44.4 g) was added dropwise at RT and the reaction mixture was stirred for 30 minutes at 60° C. The reaction mixture was cooled, filtered and the filtrate evaporated. The residue was purified by column chromatography on silica gel (eluent: $CH_2Cl_2$/$CH_3OH$ 95/5). The pure fractions were collected and the solvent evaporated, yielding 25 g (40%) of ethyl 4-[amino (hydroxyimino)methyl]-1-piperidinecarboxylate. This fraction was redissolved in 2-propanone and converted into the hydrochloric acid salt (1:1) with HCl/2-propanol. The precipitate was filtered off and dried, yielding 22 g (35%) of ethyl 4-[amino(hydroxyimino)methyl]-1-piperidine-carboxylate hydrochloride (intermediate 2).

EXAMPLE 3 a) A mixture of intermediate 2 (10.07 g), sodium ethoxide (5.42 g) and molecular sieves (45 g) in ethanol (150 ml) was stirred for 30 minutes at RT. Intermediate 1 (9.1 g) was added and the reaction mixture was stirred and refluxed for 10 hours. The reaction mixture was cooled, filtered and the filtrate evaporated. The residue was purified by column chromatography on silica gel (eluent: $CH_2Cl_2$/$CH_3OH$ 95/5). The pure fractions were collected and the solvent evaporated, yielding 11.6 g (74%) of ethyl 4- [5-(4-amino-5-chloro-2,3-dihydro-7-benzofuranyl)- 1,2,4-oxadiazol-3-yl]-1-piperidinecarboxylate (intermediate 3; mp. 162.4° C.).

b) A mixture of intermediate 3 (10 g) and potassium hydroxide (14 g) in 2-propanol (200 ml) was stirred and refluxed for 6 hours. The reaction mixture was cooled and the solvent evaporated. Water was added to the residue and evaporated again. The residue was stirred in water and the resulting precipitate was filtered off, washed with water and purified by column chromatography on silica gel (eluent: $CH_2Cl_2$/($CH_3OH$/$NH_3$) 90/10). The pure fractions were collected and the solvent evaporated, yielding 5.14 g (64%) of 5-chloro-2,3-dihydro-7-[3-(4-piperidinyl)-1,2,4-oxadiazol-5-yl]-4-benzofuranamine (intermediate 4; mp. 219.0° C.).

In the same manner as intermediate 4 was prepared from intermediate 1, 5-chloro-2,3-dihydro-2,2-dimethyl-7-[3-(4-piperidinyl)-1,2,4-oxadiazol-5-yl]-4-benzofuranamine (intermediate 5; mp. 198.8° C.) was prepared from ethyl 4-amino-5-chloro-2,3-dihydro-2,2-dimethyl-7-benzofurancarboxylate; and 2-chloro-5-methoxy-4-[3-(4-piperidinyl)-1,2,4-oxadiazol-5-yl]benzenamine (intermediate 6; mp. 160.2° C.) was prepared from ethyl 4-[5-94-amino-5-chloro-2-inethoxyphenyl-1,2,4-oxadiazol-3-yl]-1-piperidinecarboxylate.

EXAMPLE 4 a) Triethylamine (0.16 mol) was added to a solution of 4-amino-5-chloro-2,3-dihydro-7-benzofurancarboxylic acid (0.16 mol) in chloroform (600 ml) at a temperature below 10° C. Ethyl chloroformate (15.3 ml) was added afterwards and the reaction mixture was stirred for 45 minutes, while cooling on an ice-bath. Gaseous ammonia was allowed to bubble through the mixture and the reaction mixture was stirred for 3 hours at RT. The precipitate was filtered off and consecutively washed with water, 5% NaOH solution, and again water, and dried, yielding 23.5 g (69%) of 4-amino-5-chloro-2,3-dihydro-7-benzofurancarboxamide (intermediate 7).

b) Intermediate 7 (0.12 mol) was added to phosporous oxychloride (120 ml) and the reaction mixture was stirred for 45 minutes at 100° C. The mixture was cooled and the solvent evaporated. The residue was added to ice and the mixture was extracted with $CH_2Cl_2$ and methanol. The organic layer was dried over $MgSO_4$, filtered and the solvent evaporated. The residue was purified by column chromatography on silica gel (eluent: $CH_2Cl_2/CH_3OH$ 99/1). The pure fractions were collected and the solvent evaporated, yielding 14.5 g (63%) of 4-amino-5-chloro-2,3-dihydro-7-benzofuran-carbonitrile (intermediate 8).

c) A solution of hydroxylamine hydrochloride (5.3 g) in methanol (80 ml) was added to a solution of sodium (1.75 g) in methanol (80 ml). The reaction mixture was stirred for 30 minutes at RT. The precipitate was filtered off and washed with methanol (80 ml). Intermediate 8 (14.5 g) was added portionwise to the filtrate. The reaction mixture was stirred and refluxed for 7 hours. The mixture was cooled and the solvent evaporated. The residue was dissolved in 2-propanone and converted into the hydrochloric acid salt (1:1) with HCl/2-propanol. The mixture was first allowed to boil, after which it was cooled to 0° C. The precipitate was filtered off and dried, yielding 14 g (70%) of 4-amino-5-chloro-2,3-dihydro-N'-hydroxy-7-benzofurancarboximidamide monohydrochloride (intermediate 9).

d) A mixture of intermediate 9 (13.5 g), sodium ethoxide (7.5 g) and molecular sieves 4 Å (30 g) in ethanol (120 ml) was stirred for 30 minutes at RT. Ethyl 4-piperidine-carboxylate (5.2 g) was added and the reaction mixture was stirred and refluxed for 6 hours. The mixture was cooled, filtered and the filtrate was evaporated. The residue was purified by column chromatography on silica gel (eluent: $CH_2Cl_2/(CH_3OH/NH_3)$ 95/5). The pure fractions were collected and the solvent evaporated. A sample (1 g) was crystallized from $CH_3CN$. The precipitate was filtered off and dried, yielding 0.5 g (19,4%) of 5-chloro-2,3-dihydro-7-[5-(4-piperidinyl)- 1,2,4-oxadiazol-3-yl]-4-benzofuranamine (intermediate 10).

In the same manner as intermediate 10 was prepared from 4-amino-5-chloro-2,3-dihydro-7-benzofurancarboxylic acid, 5-chloro-2,3-dihydro-2,2-dimethyl-7-[5-4-piperidinyl)-1,2,4-oxadiazol-3-yl]-4-benzofuranamine (intermediate 11; mp. 230.8° C.) was prepared from 4-amino-5-chloro-2,3-dihydro-2,2-dimethyl-7-benzofuran-carboxylate.

2-chloro-5-methoxy-4-[5-(4-piperidinyl)-1,2,4-oxadiazol-3-yl]benzenamine (intermediate 12; mp. 174.2° C.) was prepared from 4-amino-5-chloro-2-methoxy-N'-hydroxy-7-benzenecarboximidamide monohydrochloride, disclosed in WO 93/02677, following the same procedure as in example 4 d).

B. Preparation of the compounds of formula (I)

EXAMPLE 5

A mixture of methyl (3-chloropropyl) ether (1.6 g), intermediate 4 (3.9 g), triethylamine (5 ml) and potassium iodide (a catalytic amount) in dimethylformamide (60 ml) was stirred for 48 hours at 60° C. The reaction mixture was cooled and the solvent evaporated. The residue was partitioned between $CH_2Cl_2$ and a saturated aqueous NaCl solution. The organic layer was separated, dried over $MgSO_4$, filtered and the solvent evaporated. The residue was purified by column chromatography on silica gel (eluent: $CH_2Cl_2/CH_3OH$ 90/10). The desired fractions were collected and the solvent was evaporated. The residue was solidified in DIPE, filtered off, dissolved in 2-propanol and converted into the hydrochloric acid salt (1:1) with HCl/2-propanol. The precipitate was filtered off and dried, yielding 1.14 g (22.1%) of 5-chloro-2,3-dihydro-7-[3-[1-(3-methoxypropyl)-4-piperidinyl]-1,2,4-oxadiazol-5-yl]-4-benzofuranamine monohydrochloride.hemihydrate (compound 1; mp. 244.3° C.).

EXAMPLE 6

A mixture of intermediate 5 (4 g), 4-bromobutanenitrile (2.2 g) and triethylamine (4.2 ml) in dimethylformamide (70 ml) was stirred for 2 hours at 70° C. The mixture was cooled and the solvent evaporated. The residue was partitioned between $CH_2Cl_2$ and $NH_3/H_2O$. The organic layer was separated, dried over $MgSO_4$, filtered and the solvent evaporated. The residue was purified by column chromatography on silica gel (eluent: $CH_2Cl_2/CH_3OH$ 95/5). The pure fractions were collected and the solvent evaporated. The residue was solidified in DIPE at 0° C., filtered and dried, yielding 1.89 g (38%) of 4-[5-(4-amino-5-chloro-2,3-dihydro-2,2-dimethyl-7-benzofuranyl)-1,2,4-oxadiazol-3-yl]-1-piperidinebutanenitrile (compound 3; mp. 151.4° C.).

EXAMPLE 7

A mixture of tetrahydrofurfuryl mesylate (2.34 g), intermediate 12 (2.7 g) and sodium carbonate (2.8 g) in 4-methyl-2-pentanone (180 ml) was stirred and refluxed for 24 hours. More tetrahydrofurfuryl mesylate (1 g) was added and the reaction mixture was stirred and refluxed for 24 hours. The reaction mixture was cooled, washed with water, dried over $MgSO_4$, filtered and the filtrate evaporated. The residue was purified by column chromatography on silica gel (eluent: $CH_2Cl_2/CH_3OH$ 95/5). The pure fractions were collected and the solvent evaporated. The residue was crystallized from $CH_3CN$. The precipitate was filtered off and dried, yielding of 1.34 g (39%) 2-chloro-5-methoxy-4-[5-[1-[(tetrahydro-2-furanyl)methyl]-4-piperidinyl]-1,2,4-oxadiazol-3-yl]-benzenamine (compound 7; mp. 148.5° C.).

TABLE

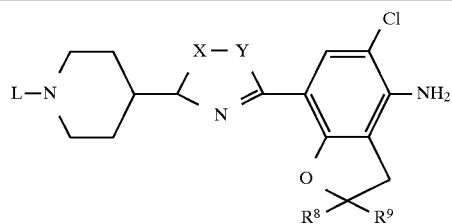

| Co. No. | Ex. No. | L | —X—Y— | $R^8$ | $R^9$ | Physical date |
|---|---|---|---|---|---|---|
| 1 | 5 | $CH_3-O-(CH_2)_3-$ | =N—O— | H | H | HCl.½H$_2$O/mp. 244.3° C. |
| 2 | 5 | $CH_3-O-(CH_2)_3-$ | —O—N= | H | H | mp. 164.7° C. |
| 3 | 6 | $NC-(CH_2)_3-$ | =N—O— | $CH_3$ | $CH_3$ | mp. 151.4° C. |
| 4 | 6 | $NC-(CH_2)_3-$ | —O—N= | $CH_3$ | $CH_3$ | mp. 158.3° C. |

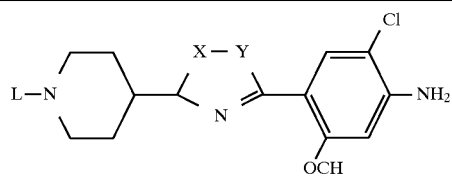

| Co. No. | Ex. No. | L | —X—Y— | Physical date |
|---|---|---|---|---|
| 5 | 6 | F—⟨⟩—O—(CH$_2$)$_3$— | —O—N= | mp. 131.0° C. |
| 6 | 6 | F—⟨⟩—O—(CH$_2$)$_3$— | =N—O— | mp. 224.8° C. |
| 7 | 6 | [tetrahydrofuran]—CH$_2$— | —O—N= | mp. 148.5° C. |
| 8 | 6 | [tetrahydrofuran]—CH$_2$— | =N—O— | mp. 136.6° C. |

C. Pharmacological example

EXAMPLE 8

Colon Motility in the Conscious Dog

Female beagle dogs, weighing 7–17 kg, were implanted with isometric force transducers, under general anaesthesia and aseptic precautions. To study the colonic motility, transducers were sutured on the colon at 8, 16, 24 and 32 cm distance from the ileo-caecal-valve. Dogs were allowed a recovery period of at least two weeks. Experiments were started after a fasting period of ±20 hours, during which water was available ad libitum. During the experiments, dogs were free to move in their cages, thanks to the telemetric (wireless) system. The cages were built in a special room, provided with glass pervious to light in one direction, i.e. the observator can see the dogs while the dogs can not see the observator. Via this system it was possible to observe the dogs for behavioral changes and to determine defecation events. The information from the transduceres was transmitted in digitized form by a small, specially built transmitter box. This box was placed in a jacket worn by the dog. The signals were received via a microphone above each cage and were transmitted to a central computer system. One of the parameters in this test is the defecation of the dogs. During the first three hours after administration of the test compound, the dogs were observed to determine whether and when defecation occurred. Compounds 1, 2 and 8 induced defecation in 60% or more of the test animals at an administration dose of 0.31 mg/kg during those first three hours.

D. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 9

Oral solutions 9 g of methyl 4hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 providing an oral solution comprising 5 mg of the A.I. per teaspoonful (5 ml). The resulting solution is filled in suitable containers.

EXAMPLE 10

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 11

Film-coated tablets

Preparation of the table core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

I claim:

1. A compound having the formula

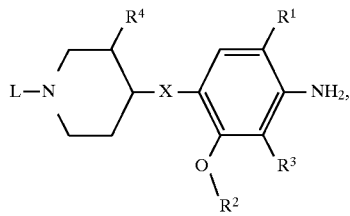

a N-oxide form, a pharmaceutically acceptable acid addition form or a stereochemically isomeric form, wherein:

$R^1$ is hydrogen or halo;

$R^2$ is $C_{1-6}$alkyl, $C_{2-6}$alkenyl or $C_{2-6}$alkynyl;

$R^3$ is hydrogen;

or $R^2$ and $R^3$ taken together may form a $C_{2-3}$alkanediyl radical wherein one or two hydrogen atoms may be replaced by $C_{1-4}$alkyl;

$R^4$ is hydrogen, hydroxy or $C_{1-6}$alkyloxy;

X is a bivalent radical of the formula

L is a radical of formula:

-Alk-$R^5$ (b),

-Alk—O—$R^6$ (c),

Alk is $C_{1-12}$alkanediyl;

$R^5$ is, cyano, $C_{1-6}$alkylcarbonyl, $C_{1-6}$alkylsulfinyl, $C_{1-6}$alkylsulfonyl, aryl, arylcarbonyl, tetrahydrofuran, dioxolane, dioxolane substituted with $C_{1-6}$alkyl, dioxane, dioxane substituted with $C_{1-6}$alkyl;

$R^6$ is hydrogen, aryl, $C_{1-6}$alkyl, hydroxy$C_{1-6}$alkyl, $C_{1-6}$alkylcarbonyl; aryl is defined as phenyl or phenyl substituted with up to three substituents selected from halo, $C_{1-6}$alkyl or $C_{1-6}$alkyloxy.

2. A compound according to claim 1 wherein $R^1$ is chloro.

3. A compound according to claim 1 wherein $R^4$ is hydrogen.

4. A compound according to claim 1 wherein $R^1$ is chloro; $R^2$ is methyl; $R^3$ and $R^4$ are hydrogen; and L is a radical of formula (b) wherein $R^5$ is tetrahydrofuran, or a radical of formula (c) wherein $R^6$ is 4-fluorophenyl.

5. A compound according to claim 1 wherein $R^1$ is chloro; $R^2$ and $R^3$ taken together form an ethanediyl radical; $R^4$ is hydrogen; and L is a radical of formula (c) wherein $R^6$ is methyl.

6. A compound according to claim 1, wherein L is a radical of formula (b) and $R^5$ is cyano or tetrahydrofuran.

7. A compound according to claim 1 wherein the compound is selected from 2-chloro-5-methoxy-4-[3-[1-[(tetrahydro-2-furanyl)methyl]-4-piperidinyl]-1,2,4-oxadiazol-5-yl]benzenamine; 5-chloro-2,3-dihydro-7-[3-[1-(3-methoxypropyl)-4-piperidinyl]-1,2,4-oxadiazol-5-yl]-4-benzofuranamine; 5-chloro-2,3-dihydro-7-[5-[1(3-methoxypropyl)-4-piperidinyl]-1,2,4-oxadiazol-3-yl]-4-benzofuranamine; the N-oxide forms, the pharmaceutically acceptable acid addition salts and the stereochemically isomeric forms thereof.

8. A composition comprising a pharmaceutically acceptable carrier and, as active ingredient, a therapeutically effective amount of a compound as claimed in any one of claims 1 to 6.

9. A process for preparing a composition as claimed in claim 6, wherein a pharmaceutically acceptable carrier is intimately mixed with a therapeutically effective amount of a compound as claimed in any one of claims 1 to 6.

10. A method for treating motility disorders of the intestinal system in patients in need of the same, which comprises administering to said patients an effective amount of a compound of claim 1.

11. A method for treating conditions related to impaired colonic transit in patients in need of the same, which comprises administering to said patients an effective amount of a compound of claim 1.

12. A method for treating motility disorders of the intestinal system in patients in need of the same, which comprises administering to said patients an effective amount of a compound of claim 2.

13. A method of treating motility disorders of the intestinal system in patients in need of same, which comprises administrating to said patients an effective amount of a compound of claim 3.

14. A method for treating motility disorders of the intestinal system in patients in need of the same, which comprises administering to said patients an effective amount of a compound of claim 4.

15. A method for treating motility disorders of the intestinal system in patients in need of the same, which comprises administering to said patients an effective amount of a compound of claim 5.

16. A method for treating motility disorders of the intestinal system in patients in need of the same, which comprises administering to said patients an effective amount of a compound of claim 7.

17. A method for treating motility disorders of the intestinal system in patients in need of the same, which comprises administering to said patients an effective amount of a compound of claim 6.

18. A process for preparing a compound as claimed in claim 1 comprising alkylating an intermediate of formula (II)

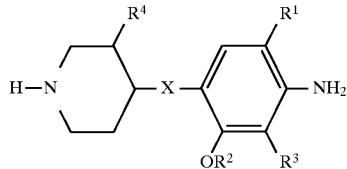

(II)

a stereochemically isomeric form, or a pharmaceutically acceptable acid addition salt thereof wherein $R^1$, $R^2$, $R^3$, $R^4$ and X are as defined in claim 1, with an intermediate of formula (III), L-W$^1$(III)

wherein L is as defined in claim 1 and $W^1$ is a leaving group, and optionally converting the compounds of formula (I) into each other by a functional group transformation reaction; and, optionally converting a compound of formula (I) into a pharmaceutically acceptable acid addition salt or converting an acid addition salt into a free base form with alkali; and/or preparing stereochemically isomeric forms thereof.

19. An intermediate of formula

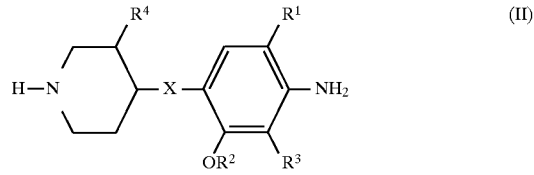

(II)

a stereochemically isomeric form, or a pharmaceutically acceptable acid addition salt thereof wherein $R^1$, $R^2$, $R^3$, $R^4$ and X are as defined in claim 1.

* * * * *